United States Patent
Takayoshi et al.

(10) Patent No.: US 7,831,136 B2
(45) Date of Patent: Nov. 9, 2010

(54) OPTHALMIC PHOTOGRAPHY APPARATUS

(75) Inventors: Suzuki Takayoshi, Hamamatsu (JP); Yoshizawa Itaru, Tokyo (JP)

(73) Assignee: Kowa Kabushiki Kaisha (JP)

( * ) Notice: Subject to any disclaimer, the term of this patent is extended or adjusted under 35 U.S.C. 154(b) by 272 days.

(21) Appl. No.: 11/988,988

(22) PCT Filed: Jul. 24, 2006

(86) PCT No.: PCT/JP2006/314542

§ 371 (c)(1), (2), (4) Date: Jan. 17, 2008

(87) PCT Pub. No.: WO2007/013383

PCT Pub. Date: Feb. 1, 2007

(65) Prior Publication Data

US 2009/0263115 A1 Oct. 22, 2009

(30) Foreign Application Priority Data

Jul. 27, 2005 (JP) ............................. 2005-217759

(51) Int. Cl.
G03B 29/00 (2006.01)
G03B 17/00 (2006.01)
H04N 5/222 (2006.01)
A61B 3/14 (2006.01)

(52) U.S. Cl. .................. 396/18; 396/51; 348/333.03; 351/206

(58) Field of Classification Search ............... 396/18
See application file for complete search history.

(56) References Cited

U.S. PATENT DOCUMENTS

2001/0028438 A1  10/2001  Matsumoto ............ 351/206
2005/0024586 A1   2/2005  Teiwes et al. ......... 351/209

FOREIGN PATENT DOCUMENTS

JP   59090547   5/1984
JP   59164033   9/1984

(Continued)

OTHER PUBLICATIONS

Machine English Translation JP 2005-095474, Kato Yasuo, Apr. 14, 2005, A16B 3/14, 25 pages.*

(Continued)

*Primary Examiner*—Melissa J Koval
(74) *Attorney, Agent, or Firm*—Adams & Wilks

(57) ABSTRACT

An ocular fundus is photographed as an electronic image via photographic stops, and the image of the photographed ocular fundus is recorded in a recording apparatus. The photographic stops are selected by moving a movable stop unit. Alignment observation or monocular photography is performed when a center photographic stop is selected. Left and right images for stereoscopic viewing are acquired when left and right photographic stops are selected. The acquired ocular fundus images are recorded in association with the position of the photographic stop used when the images were acquired. Therefore, the left image can be displayed on the left side of the monitor and the right image can be displayed on the right side by referring to the information of the photographic stop position when the left and right images for stereoscopic viewing are displayed on the monitor. This makes reliable stereoscopic viewing of the ocular fundus possible.

21 Claims, 12 Drawing Sheets

FOREIGN PATENT DOCUMENTS

| | | |
|---|---|---|
| JP | 02005922 | 1/1990 |
| JP | 05245109 | 9/1993 |
| JP | 05305059 | 11/1993 |
| JP | 10075932 | 3/1998 |
| JP | 2002017681 | 1/2002 |
| JP | 2003230540 | 8/2003 |
| JP | 2002097648 | 4/2004 |
| JP | 2004135941 | 5/2004 |
| JP | 2005095474 | 4/2005 |
| JP | 2005312764 | 11/2005 |

OTHER PUBLICATIONS

Machine English Translation JP 2005-312764, Kusushiro Tsuguo, Nov. 10, 2005, A16B 3/14, 14 pages.*

Machine English Translation JP 2003-230540, Kitamura Takeshi, Aug. 19, 2003, A16B 3/14, 15 pages.*

* cited by examiner

OPTHALMIC PHOTOGRAPHY APPARATUS

CROSS-REFERENCE TO RELATED APPLICATIONS

This application is a U.S. national stage application of International Application No. PCT/JP2006/314542, filed Jul. 24, 2006, claiming a priority date of Jul. 27, 2005, and published in a non-English language.

TECHNICAL FIELD

The present invention relates to an ophthalmic photography apparatus, and more specifically to an ophthalmic photography apparatus for acquiring an image that allows stereoscopic viewing of the ocular fundus.

BACKGROUND ART

Conventionally, the stereo shape of the ocular fundus must be viewed in order to diagnose glaucoma. Stereo photographs, i.e., two (a plurality of) images that have a parallax with respect to the same subject-eye, are taken and displayed in pairs to thereby view the subject's eye stereographically.

A fundus camera that can take an image having a parallax is provided with a photographic stop (two-aperture stop) having two left and right stops (apertures) that is positioned in conjugate with the anterior ocular segment of the subject's eye (in conjugate with the pupil) relative to the objective lens, and a beam of light that has passed through each of the apertures from the ocular fundus is received as left and right images on the film surface or on the image surface of an imaging device to obtain an image for stereoscopic viewing.

With such a fundus camera, photography from one aperture of a photographic stop is switched to photography from the other aperture in accordance with the operation of a shutter to acquire two left and right images in succession (Patent Document 1). Alternatively, a first image is taken with a single shot, a second image is then acquired in a sequential manner, and the images are alternately displayed on a monitor (patent Document 2).

Also known are a fundus camera (Patent Document 3) that is provided with a photographic stop having an ordinary aperture stop and a two-aperture stop for stereographic photography, in which the ordinary aperture stop is enabled during observation to carry out observations, and the two-aperture stop is enabled during stereographic photography to carry out photography; a fundus camera for stereoscopic viewing (Patent Document 4) wherein the spacing of two apertures for bisecting a beam of light that has passed through an objective lens is varied in accordance with the pupil diameter; a fundus camera (Patent Document 5) in which a ring slit that restricts illumination light and a two-aperture stop (photographic stop) are switched in conjunction for two use for binocular photography and monocular photography; and a fundus camera (Patent Document 6) in which the ring slit and the stop can be switched simultaneously in accordance with the photographic magnification during photography.

Also known is a configuration in which photographic condition information such as information of the photographed left and right eyes are recorded and stored in association with the photographic image (Patent Document 7), or in which the position of a fixation lamp is sequentially varied, the ocular fundus is stereographically or panoramically photographed from various angles, and the images are recorded in association with the position of the fixation lamp (Patent Document 8).

Also known is a fundus camera (Patent Document 9) in which the image of the ocular fundus is temporarily stored in high-speed memory, and the recorded image of the ocular fundus is transferred to an external low-speed recording apparatus at a transfer timing that corresponds to the photography mode, thereby making continuous photography of the ocular fundus possible.

Patent Document 1: JP-A 1984-90547
Patent Document 2: JP-A 1998-75932
Patent Document 3: JP-A 1984-164033
Patent Document 4: JP-A 1990-5922
Patent Document 5: JP-A 1993-245109
Patent Document 6: JP-A 1993-305059
Patent Document 7: JP-A 2002-17681
Patent Document 8: JP-A 2004-135941
Patent Document 9: JP-A 2004-97648

PROBLEMS TO BE SOLVED

However, with a conventional stereo photographic fundus camera, two left/right parallax images are not combined and stored in association as a set. Therefore, the user must himself select the parallax images individually and arrange them in left and right positions for image composition, which is laborious and the cause of errors.

On the other hand, an internal fixation lamp is shown to a patient via one aperture of the two-aperture stop prior to photography, but the internal fixation lamp is not visible to the patient depending on the lighted position of the selected internal fixation lamp, and the significance of the internal fixation lamp is lost. To solve this problem, the external shape of the photographic lens must be increased more than necessary, and unnecessary costs are disadvantageously incurred.

Besides, there are displays that switch between a two-dimensional screen and a three-dimensional screen, but there is a problem in that it is difficult to operate a personal computer (to file images) while making stereoscopic observations. Furthermore, there is a problem in that the mechanism for projecting the focus marker on the ocular fundus is complicated in a fundus camera that switches the photographic stop for successive photography.

The present invention was conceived in view of the foregoing, and an object of thereof is to provide an ophthalmic photography apparatus that can easily and reliably acquire images for stereoscopic viewing of the ocular fundus.

SUMMARY OF THE INVENTION

The present invention for solving the problems is characterized by an ophthalmic photography apparatus comprising:

imaging means for photographing a subject's eye as an electronic image via a photographic stop;

recording means for recording a photographed subject-eye image; and selection means for switching the photographic stop and selecting a photographic stop that is in a different position, wherein the subject's eye is sequentially photographed in a single shutter operation via photographic stops that are in different positions to thereby acquire a plurality of images of the subject's eye, and each of the acquired subject-eye images is recorded in the recording means in association with the position of the photographic stop used when the image is acquired.

The present invention is also characterized by an ophthalmic photography apparatus having first and second photography modes, comprising:

imaging means for photographing a subject's eye as an electronic image via a photographic stop; and selection means for switching the photographic stop and selecting a photographic stop that is in a different position, wherein, when the first photography mode has been selected, the subject's eye is photographed in a single shutter operation via the photographic stop that is in a first position to thereby acquire a single image of the subject's eye, and, when the second photography mode has been selected, the photographic stop that is in a second and third position is selected, and the subject's eye is photographed in a single shutter operation via selected one of photographic stops and subsequently via the other photographic stop to thereby acquire two images of the subject's eye.

The present invention is further characterized by an ophthalmic photography apparatus having first, second, and third photography modes, comprising:

imaging means for photographing a subject's eye as an electronic image via a photographic stop; and selection means for switching the photographic stop and selecting a photographic stop that is in a different position, wherein, when the first photography mode has been selected, the subject's eye is photographed in a single shutter operation via the photographic stop that is in a first position to thereby acquire a single image of the subject's eye; when the second photography mode has been selected, the photographic stop that is in a second and third position is selected, and the subject's eye is photographed in a single shutter operation via selected one of photographic stops and subsequently via the other photographic stop to thereby acquire two images of the subject's eye; and, when the third photography mode has been selected, the photographic stop that is in a first, second, and third position is selected, and the subject's eye is photographed in a single shutter operation via selected one of photographic stops, subsequently via remaining one of photographic stops, and then via the other remaining photographic stop to thereby acquire three images of the subject's eye.

EFFECT OF THE INVENTION

According to the present invention, the subject's eye is sequentially photographed in a single shutter operation via the photographic stops that are in different positions. The images of the subject's eye thus photographed are recorded and stored in association with the position of the photographic stop used when the images are acquired. Therefore, photographs can be taken in a simple manner in a stereoscopic photography mode, and the position information of the photographic stop is referenced when the recorded images are reproduced. This allows the images of the subject's eye to be displayed in an optimal manner. For example, the two images of the subject's eye that were acquired by stereoscopic photography (second photography mode) can be aligned left and right and displayed by using the position information of the photographic stop. When three consecutive photographs (third photography mode) are taken, three images of the subject's eye are repeatedly displayed one by one in a stereographic video. Therefore, the subject's eye can be stereoscopically viewed in a favorable manner.

KEY TO SYMBOLS

Figure 1:
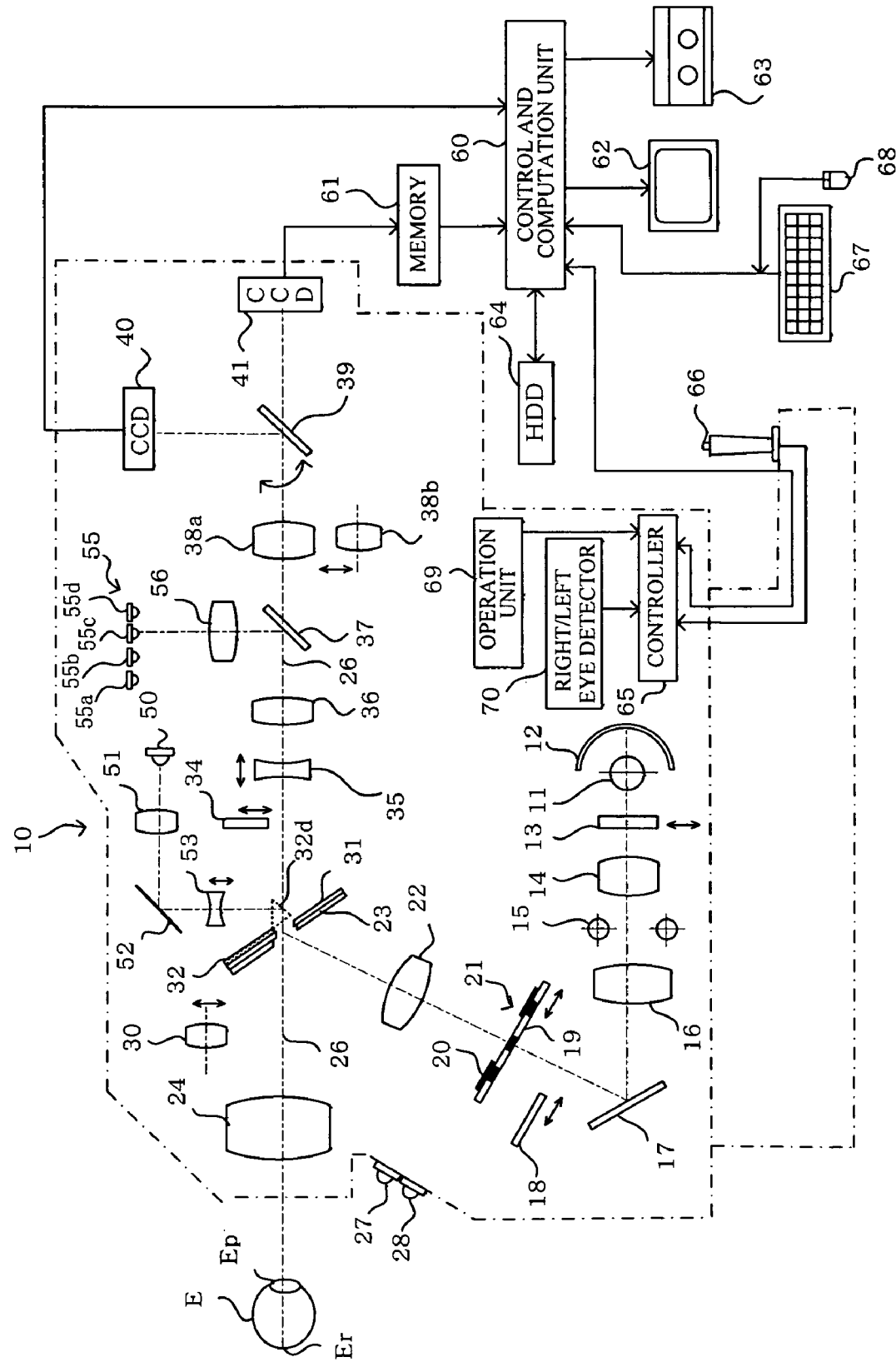
FIG. 1 is a block diagram showing the optical system of an ophthalmic photography apparatus according to the present invention.

13 Visible light cutting/infrared light transmitting filter
15 Strobe
21 Ring slit
23 Apertured total reflection mirror
30 Anterior ocular segment lens
31 Fixed stop
32 Movable stop unit
50 Focus-marker light source
55 Internal fixation lamp
63, 90 Stereo monitor

DETAILED DESCRIPTION OF THE INVENTION

Embodiments of the present invention are described in detail below with reference to the drawings.

Embodiments

In FIG. 1, an ophthalmic photography apparatus of the present invention comprises a fundus camera 10 that photographs the ocular fundus of the subject's eye, recording apparatuses (recording means) 61 and 64 that record images of the photographed ocular fundus, monitors 62 and 63 that display images of the photographed ocular fundus or images of the recorded ocular fundus, and other components. The fundus camera 10 enclosed and depicted by the alternate long and short dash line is provided with an observation lamp 11 that emits infrared and visible illumination light and is disposed in the center of the curvature of a spherical mirror 12. The light from the observation lamp 11 and the spherical mirror 12 travels though a visible light-cutting/infrared light-transmitting filter 13 that is removably disposed in the optical path, a condenser lens 14, a strobe light 15 as a photographic light source, and a condenser lens 16, and is then incident on the total reflection mirror 17.

The illumination light reflected by the total reflection mirror 17 is transmitted through a relay lens 22 via a ring slit 21 used as an illumination stop that is composed of a movable shield plate 19 and a fixed stop 20, is reflected by an apertured total reflection mirror 23, and is incident on an anterior ocular segment (pupil) Ep of a subject's eye E via an objective lens 24. The ring slit 21 is disposed in the illumination optical system at a position substantially conjugate with the anterior ocular segment Ep (pupil) of the subject's eye. The movable shield plate 19 is composed of a transparent glass plate, and circular shield sections 19a, 19b, and 19c are formed on the movable shield plate 19 in the manner shown in FIGS. 5A, 5B, and 5C. The fixed stop 20 is an aperture stop having a centrally disposed aperture 20a, and patterns of illumination light can be obtained in accordance with the position of the illumination stop 19 because the shield sections 19a, 19b, and 19c move into the aperture 20a in accordance with the movement of the movable shield plate 19.

An exciter filter 18 is inserted into or removed from the optical path of the illumination optical system during fluorescence photography.

A light source 27 composed of an infrared LED (light-emitting diode) for illuminating the anterior ocular segment Ep with infrared light is provided in order to be used when alignment is performed with the anterior ocular segment, and a light source 28 composed of an LED for illuminating the anterior ocular segment with weak white light is provided in order to photograph the anterior ocular segment.

Reflected light from the eye fundus Er illuminated by illumination light that has passed through the ring slit 21 is transmitted through the objective lens 24, the apertured total reflection mirror 23, a fixed stop 31, a movable stop unit 32, a focusing lens 35, an imaging lens 36, a half mirror 37, and a variable power lens 38a, and is incident on a return mirror 39. When the return mirror 39 is positioned as shown, light reflected from the ocular fundus is incident on an infrared light-sensitive CCD (imaging means) 40 that is in a position conjugate with the ocular fundus, and the CCD 40 forms an image of the ocular fundus. When the return mirror 39 is removed from the optical path, reflected light from the ocular fundus is incident on a visible light-sensitive CCD (imaging means) 41 that is conjugate with the ocular fundus, and an image of the ocular fundus is photographed by the CCD 41.

Figure 2A:
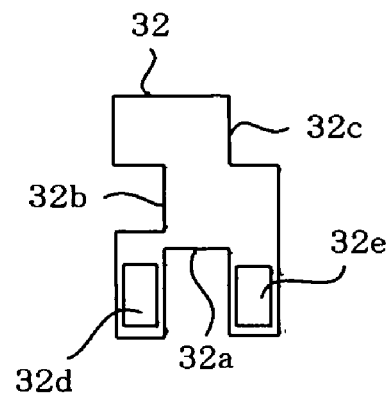
FIG. 2A is a plan view showing the configuration of a movable stop unit.
Figure 2B:
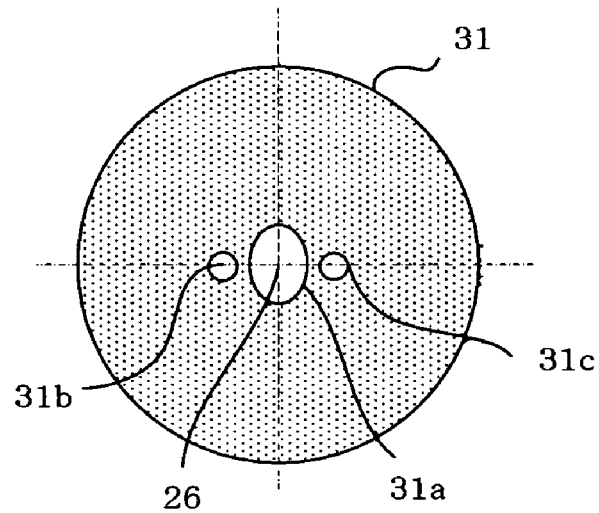
FIG. 2B is a plan view showing the configuration of a fixed stop.
Figure 2C:
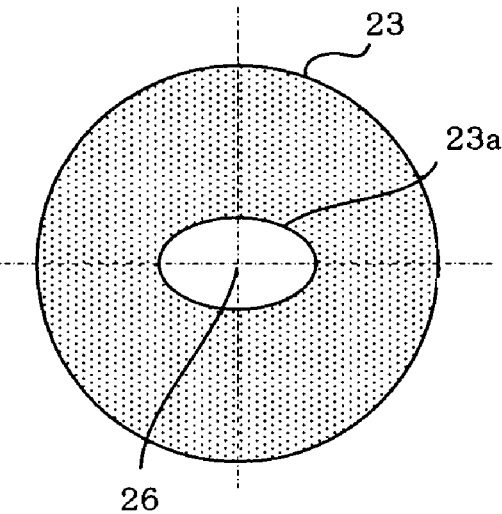
FIG. 2C is a plan view showing the configuration of an apertured total reflection mirror.

The apertured total reflection mirror 23 is a circular total reflection mirror provided with a centrally disposed horizontally elliptical aperture 23a, as shown in FIG. 2C. As shown in FIG. 2B, the fixed stop 31 is a stop provided with a centrally disposed monocular photographic stop 31a and with bilaterally disposed photographic stops (two-aperture stop) 31b and 31c for projecting a focus marker and performing stereoscopic photography. The fixed stop 31 is circular in shape, has substantially the same size as the apertured total reflection mirror 23, is centrally aligned with the apertured total reflection mirror 23, and is affixed tightly and securely to the apertured total reflection mirror 23. The photographic stops 31a, 31b and 31c are provided at positions substantially conjugate with the anterior ocular segment (pupil) of the subject's eye. In this case, the center of the photographic stop 31a is disposed in a position (first position) that coincides with an optical axis 26 of the objective lens 24 (optical axis of the photographic optical system). To produce right and left images for stereoscopic viewing, the photographic optical path is laterally split at a position conjugate with the pupil. The photographic stop 31b is disposed on the left side (second position) of the divided optical path, and the photographic stop 31c is disposed on the right side (third position) of the divided optical path. The aperture 23a of the apertured total reflection mirror 23 has a size that allows the apertures of the photographic stops 31a, 31b, and 31c to be contained within the aperture 23a when the centers of the apertured total reflection mirror 23 and fixed stop 31 are in alignment.

Figure 4:
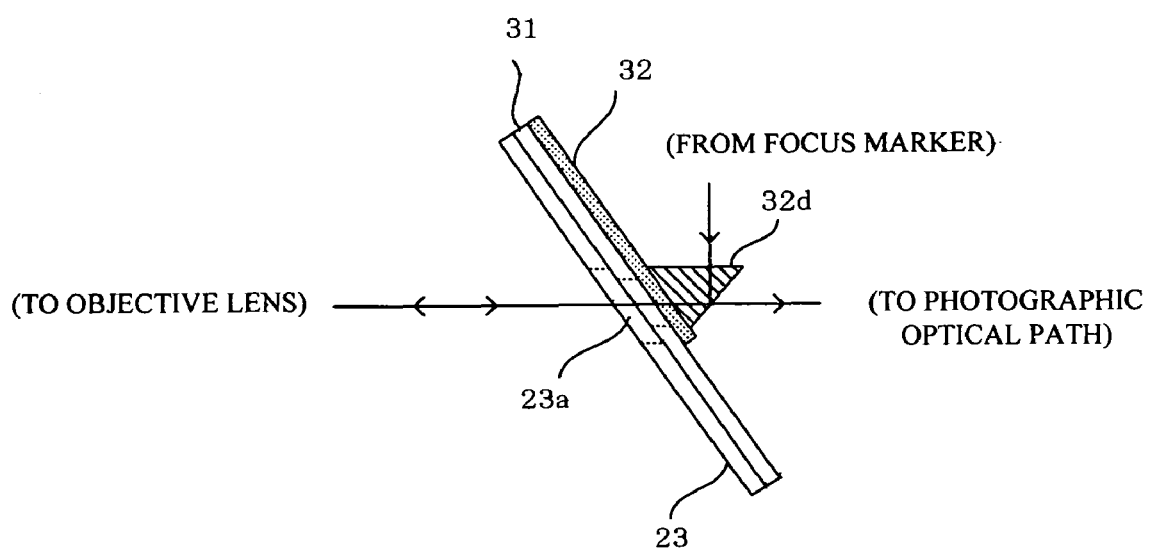
FIG. 4 is an illustrative view showing in detail the pathway of light rays that pass through the photographic stop.

As shown in FIG. 2A, the movable stop unit 32 has a notched section 32a for photographic light during monocular photography, a notched section 32b for the left side optical path during stereoscopic photography, and a notched section 32c for the right side optical path during stereoscopic photography. Reflection prisms 32d and 32e (also see FIG. 4) are provided on both sides of the notched section 32a to reflect a focus marker toward the eye fundus.

The movable stop unit 32 is moved by a controller 65 in a vertical direction above the fixed stop 31 in accordance with the photography mode, as described below. When the movable stop unit 32 moves to the position shown in FIG. 3A, the notched section 32a opens the aperture of the photographic stop 31a and selects the photographic stop 31a. When the movable stop 32 moves to the positions shown in FIGS. 3B and 3C, the notched sections 32b and 32c open the apertures of the photographic stops 31b and 31c, respectively, and select the photographic stop 31b or 31c. In this manner, the controller (selection means) 65 changes the photographic stop by causing the movable stop unit 32 to move in a sequential manner, and selects one of the stops, i.e., the photographic stop 31a in the first position, the photographic stop 31b in the second position, or the photographic stop 31c in the third position. For example, when a single image is acquired, such as in monocular photography, the photographic stop 31a is selected; when a right-left pair of images is acquired, such as in stereoscopic photography, the photographic stops 31b and 31c are selected; and in the case of three consecutive photographs, the photographic stops 31a, 31b and 31c are selected.

Figure 3A:
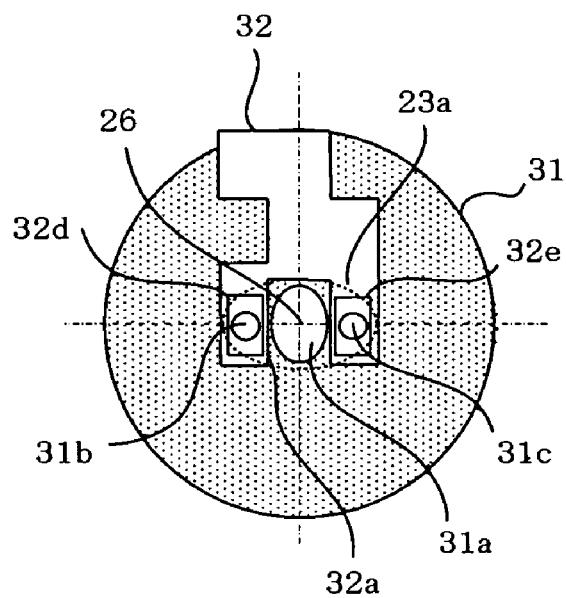
FIG. 3A is an illustrative view at the time the movable stop unit is moved upward and three apertures of the photographic stop have been selected.
Figure 3B:
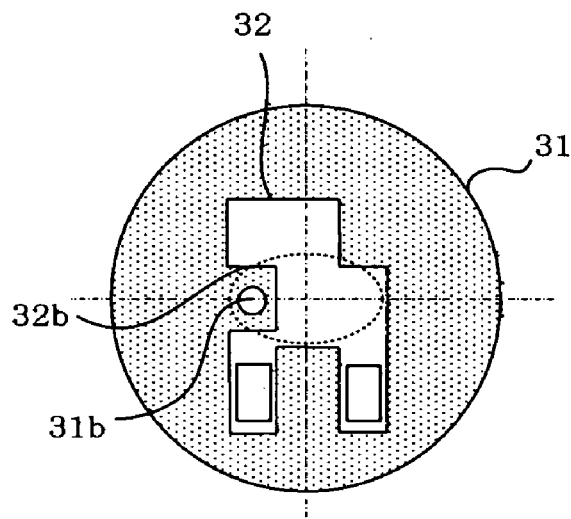
FIG. 3B is an illustrative view at the time the movable stop unit is moved to the center and the left-side aperture of the photographic stop has been selected.
Figure 3C:
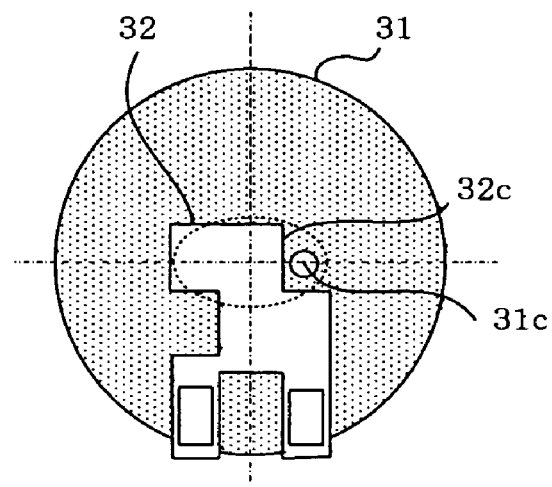
FIG. 3C is an illustrative view at the time the movable stop unit is moved downward and the right-side aperture of the photographic stop has been selected.
Figure 5A:
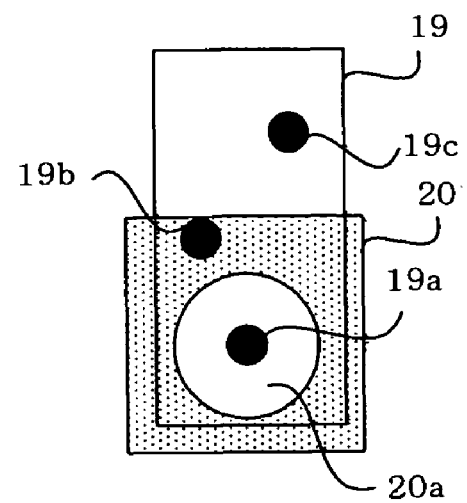
FIG. 5A is an illustrative view at the time the illumination stop is switched to monocular photography.
Figure 5B:
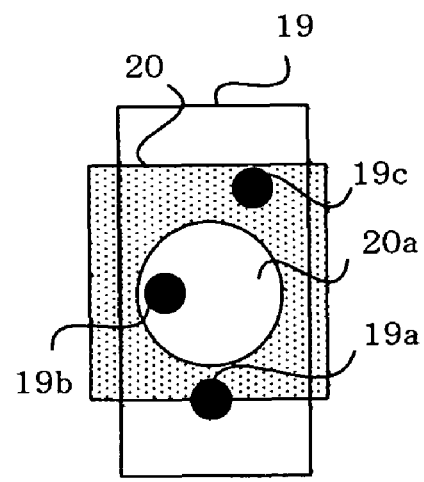
FIG. 5B is an illustrative view at the time the illumination stop is switched to stereoscopic photography.
Figure 5C:
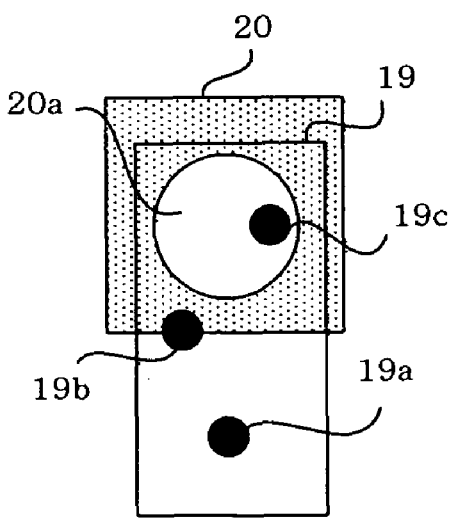
FIG. 5C is an illustrative view at the time the illumination stop is switched to stereoscopic photography.

When the movable stop unit 32 is moved to the positions shown in FIGS. 3A, 3B, and 3C, the controller 65 causes the movable shield plate 19 of the ring slit 21 to move in conjunction with the movable stop unit to the positions shown in FIGS. 5A, 5B, and 5C. The illumination stop is switched to the illumination stop (FIG. 5A) in which a shield section 19a comes to the center of the aperture 20a when the photographic stop is switched to the photographic stop 31a; and the illumination stop is switched to the illumination stop (FIGS. 5B and 5C) in which a shield section comes to the left and right sides of the aperture 20a, when a switch has been made to the photographic stops 31b and 31c.

Returning to FIG. 1, an anterior ocular segment lens 30 is removably inserted in the optical path between the objective lens 24 and the apertured total reflection mirror 23. When the anterior ocular segment lens 30 is inserted into the optical path, an image of the anterior ocular segment Ep illuminated by the illumination light source 27 is captured in the CCD 40, and alignment is performed using the image of the anterior ocular segment Ep.

The fundus camera is also provided with a focus marker projecting optical system in order to facilitate bringing the ocular fundus into focus. In the projecting optical system, marker light from a focus-marker light source 50 composed of an infrared LED is transmitted through a lens 51, a mirror 52, and a lens 53. The optical path is then bisected by the reflection prisms 32d and 32e fixed in place to the movable stop unit 32, and the marker light is projected onto the ocular fundus Er. In this case, the markers are designed so that their images reflected by the reflection prisms 32d and 32e form a single point when the ocular fundus is in focus, while being are separated when out of focus. When the focusing lens 35 is moved in order to adjust the focus, the position of the lens 53 is moved in conjunction therewith, and the separated state of the markers on the ocular fundus Er changes. Therefore, an examiner can bring the ocular fundus into focus by observing the images of the focus marker.

A barrier filter 34 is inserted on the subject's eye side of the focusing lens 35 during fluorescence photography.

An internal fixation lamp 55 composed of a plurality of fixation lamps 55a through 55d is provided in order to cause the subject's eye to fixate on the fundus camera. One of the fixation lamps 55a through 55d is turned on depending on whether the subject's eye to be photographed is the left or right eye, and depending on the photographing position of the ocular fundus (a position near or distant from a papilla or the like). The light from the lighted fixation lamp passes through a lens 56; is reflected by the half mirror 37; passes through the photographic lens 36, the focus lens 35, the photographic stop 31a (31b, 31c), the apertured mirror 23, and the objective lens 24; and is projected onto the ocular fundus Er. The subject's eye can therefore be kept at a predetermined position with respect to the fundus camera by having the patient fixate on the internal fixation lamp. In the drawings, the fixation lamps 55a through 55d are shown as being placed side-by-side on the page surface. However, in actual use, the fixation lamps are placed perpendicular to the page space.

The CCD 40 forms an image of the ocular fundus illuminated by infrared light that has passed through the visible light cutting/infrared light transmitting filter 13, or an image of the anterior ocular segment illuminated by infrared light from the light source 27. The image is inputted to a control and computation unit 60, which is composed of a CPU or the like, and the resulting image is displayed as a video image on an ordinary monitor (first display apparatus) 62. The examiner can view the image displayed on the monitor 62 and perform alignment and adjust the focus. A stereo monitor (second display apparatus) 63 is provided as a dedicated display for stereoscopic viewing. The examiner can stereoscopically view the ocular fundus by observing the right and left images via the stereo monitor 63.

The CCD 41 photographs a still image of the ocular fundus illuminated by the strobe light 15 when a shutter switch 66 is operated. The image of the ocular fundus is temporarily stored in a high-speed memory (first recording means) 61 and is recorded (filed) via the control and computation unit 60 in second recording means, which is implemented using a low-speed hard disk (HDD) 64 as an external recording device, or is displayed on the monitor 62 or stereo monitor 63.

A keyboard 67, mouse 68, or other input means is also provided, and various data can be inputted via these input devices.

The controller 65 composed of a CPU or the like is provided to the fundus camera. The controller 65 connects to the control and computation unit 60 for mutual signal exchange, controls the removal of the return mirror 39 from the optical path when the shutter switch 66 is operated, and also causes the strobe light 15 to emit a suitable amount of light. The controller 65 additionally controls the insertion and removal of the visible light cutting/infrared light transmitting filter 13, exciter filter 18, barrier filter 34, anterior ocular segment lens 30, and variable power lenses 38a and 38b into and from the optical path, and also controls the movement of the movable stop unit 32 and the movement of the movable shield plate 19.

An operation unit (operation panel) 69 is also provided to the fundus camera. The operation unit 69 has a photography mode selection switch for selecting between a monocular photography mode, a stereoscopic photography mode, and a mode in which three consecutive images are photographed; an anterior ocular segment lens insertion/removal switch; a photographing position selection switch; and the like. Information related to the switches selected using the operation unit 69 is inputted to the controller 65.

A right/left eye detector 70 for detecting whether the subject's eye to be photographed is the left or right eye is furthermore provided, and the detected information concerning whether the eye is the left or right eye is inputted to the controller 65.

Figure 6A:
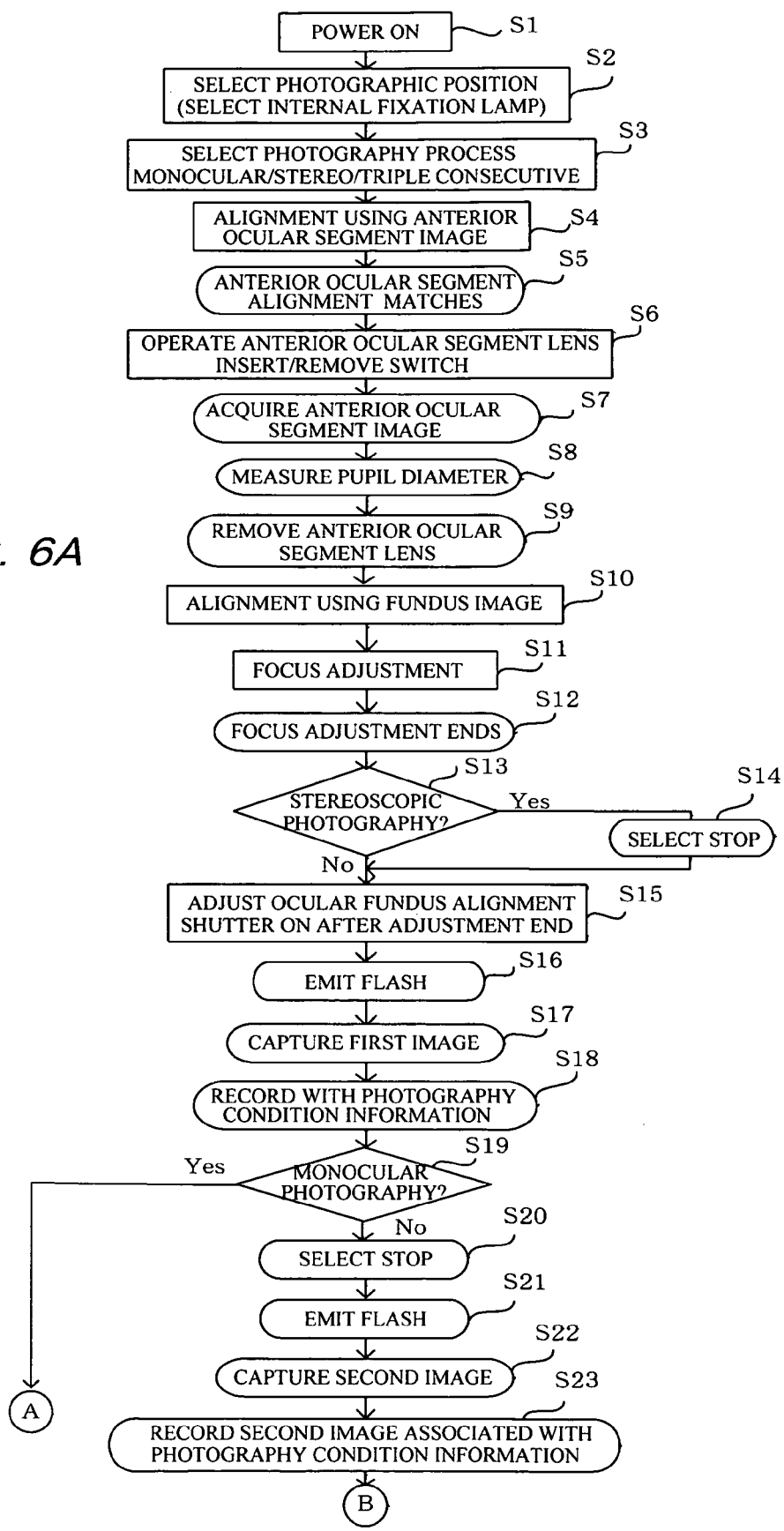
FIG. 6A is a flowchart showing the sequence in which the photography mode is selected for fundus photography.

The operation of the apparatus in such a configuration will be described in accordance with the flow shown in FIGS. 6A and 6B. In the drawings, the rectangular blocks are steps that involve examiner operation, the blocks having left and right rounded ends are steps that involve automatic operation by the apparatus, and the rhombic blocks are items determined by the apparatus.

The power is switched on in step S1. At this point, initial settings are as follows: the movable stop unit 32 is in the position shown in FIG. 3A, the photographic stop 31a is selected, the anterior ocular segment lens 30 is inserted in the optical path, and the visible light-cutting/infrared light-transmitting filter 13 is inserted in the optical path. The fundus camera is moved to a position that allows the right eye or the left eye to be photographed in accordance with whether the subject's eye to be photographed is the right eye or the left eye. Since the right/left eye detector 70 detects the eye to be photographed, a signal that indicates whether the subject eye is the left eye or the right eye is inputted to the control unit 65.

First, the examiner selects a position (location) of the ocular fundus to be photographed using the photographing position selection switch of the operation unit 69 (step S2). The person being examined fixates on the lighted fixation lamp because the control unit 65 has selected and lighted one of the fixation lamps 55a to 55d on the basis of the selected photographing position information and the information from the right/left eye detector 70.

Next, the photography mode selection switch provided to the operation unit 69 is used to select (step S3) the monocular photography mode (first photography mode), the stereoscopic photography mode (second photography mode), or the mode in which three consecutive images are photographed (third photography mode), and the resulting information is inputted to the control unit 65.

Next, the light source 27 is turned on, the anterior ocular segment illuminated by the light source 27 is imaged by a CCD 40 via the anterior ocular segment lens 30, the resulting image is displayed on the monitor 62, and the alignment of the anterior ocular segment is initiated (step S4). When alignment of anterior ocular segment is completed (step S5), the anterior ocular segment insertion/removal switch is operated (step S6), a light source 28 is lighted in place of the illumination light source 27 in synchronization therewith, and the return mirror 39 is removed from the optical path. Therefore, the anterior ocular segment is imaged by a CCD 41 (step S7) and the resulting image is stored in memory 61.

The control and computation unit 60 processes the image of the anterior ocular segment that is stored in the memory 61, the pupil diameter is calculated (step S8), the spectral distribution is detected, and a determination is made as to whether the iris is blue (blue color) or brown (brown color). Next, the anterior ocular segment lens 30 is removed from the optical path (step S9).

Since the monocular photographic stop 31a is selected as the initial setting, the illumination stop is one in which the shield section 19a is at the center of the aperture 20a of the fixed stop 20, as shown in FIG. 5A. The light from the ocular fundus illuminated by infrared light via the illumination stop is transmitted through the aperture 23a of the apertured total reflection mirror 23 and the monocular photographic stop 31a, an image is created by the CCD 40, and the image is displayed on the monitor 62. Therefore, the examiner observes the fundus image and performs alignment (step S10).

The focus marker light source 50 is lighted at this time, and the marker light is bisected by the reflection prisms 32d and 32e of the movable stop unit 32 and projected onto the ocular fundus. The lens 53 is moved in accordance with the movement of the focusing lens 35, and the separation of the marker images varies on the ocular fundus as the examiner operates the focusing lens 35. Therefore, the examiner operates the focusing lens to adjust the focus until the marker images match, and he thus brings the ocular fundus into focus (step S11).

When the focus has been adjusted (step S12), a determination is made as to whether it is the stereoscopic photography (step S13). The apparatus may detect the matching of the marker images, determine the completion of focus adjustment and lock the focus in order to advance from step S12 to S13. Alternatively, if the examiner determines that focusing is complete, the process may be caused to advance from step S12 to step S13 by operating a focus end button (or focus lock) that is not depicted in the drawings. Since the current mode is the monocular photography mode, the process advances directly to step S15, ocular fundus alignment is performed, and the shutter switch 66 is operated when ocular fundus alignment is completed. The return mirror 39 is removed from the optical path in synchronization with the shutter operation, and a strobe light (flash) 15 is emitted (step S16). The amount of luminous energy is determined by the pupil diameter obtained in step S8, the selected photographic stop, the position of the lighted fixation lamp, the color of the iris, and the photographic magnification. The examiner can correct the amount of luminous energy.

The eye fundus image thus illuminated by the light of the strobe light 15 passes via the photographic stop 31a through the focusing lens 35, the imaging lens 36, and the variable power lens 38a, and is formed in the CCD 41. Thus, the ocular fundus image is acquired as a first image (step S17). The ocular fundus image is then temporarily recorded in the memory 61 (step S18). In this case, the ocular fundus image is recorded so that it is associated with photographic conditions such as the ID of the subject's eye, the time and date of photography, the amount of light used in the photography (amount of light emitted by the strobe light), an indication of the left or right eye, the position of the photographic stop, and the like.

Figure 6B:
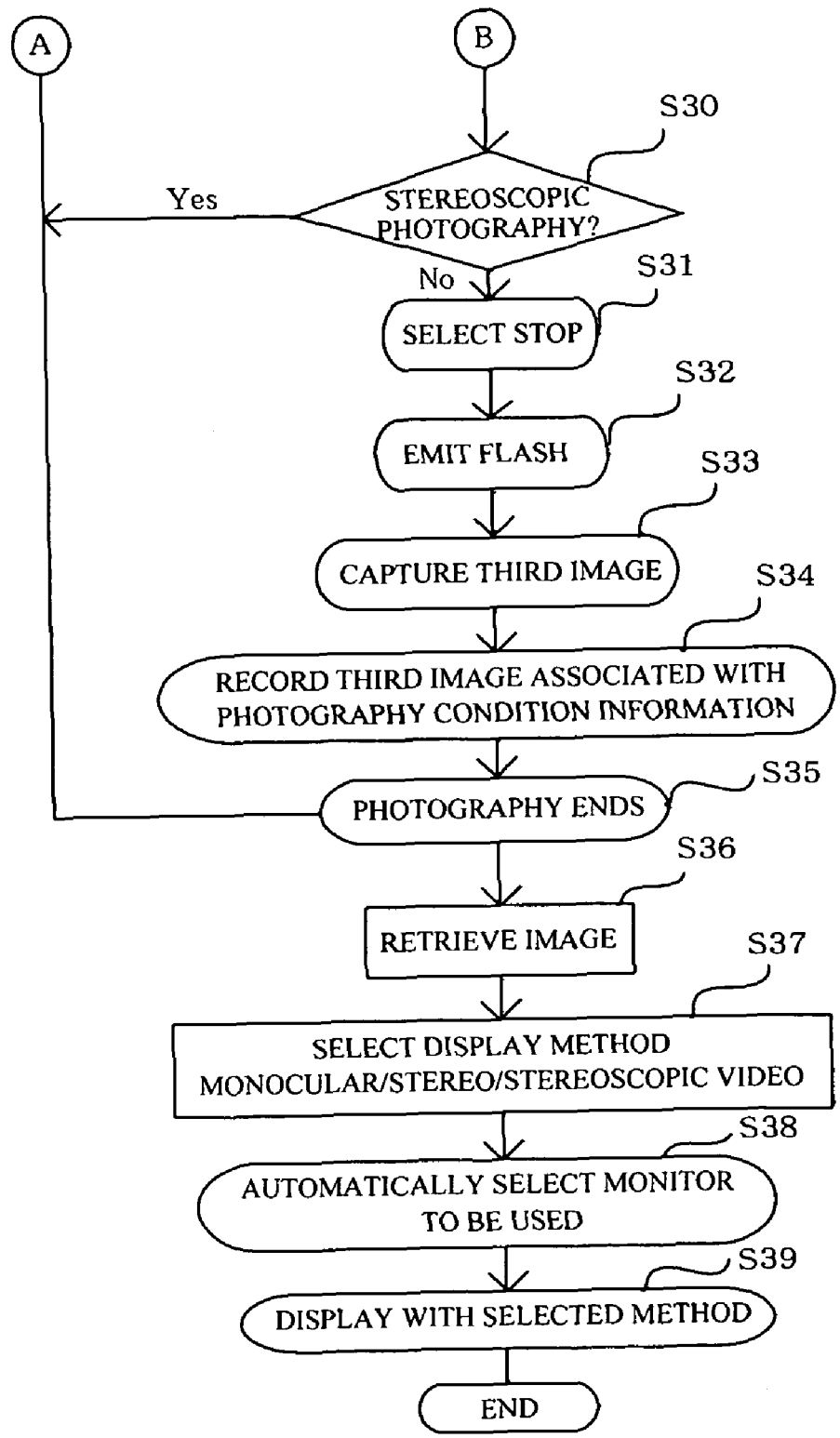
FIG. 6B is a flowchart that continues from FIG. 6A and shows the sequence in which the photography mode is selected for fundus photography.

Next, a determination is made in step S19 as to whether it is the monocular photography, and since the current mode is monocular photography, the process advances to step S35 of FIG. 6B and photography is ended.

In this manner, the ocular fundus image is acquired via the photographic stop 31a by a single shutter operation (step S15) in monocular photography, and the image is associated with photography condition information and is recorded in the memory 61.

On the other hand, when stereoscopic photography (stereo photography) is selected in step S3, step S13 is affirmed upon completion of ocular fundus alignment. Therefore, the process advances to step S14 and the photographic stop 31b or 31c is selected in place of the photographic stop 31a. In this case, if the movable stop unit 32 moves to select the photographic stop after the shutter is operated in step S15, then time will be lost. Therefore, the photographic stop is preferably positioned in advance at a stage prior to shutter operation. However, when the photographic stop is positioned at a position other than the center position (31a), the examiner may no longer be able to see the internal fixation lamp during alignment. In order to prevent the above situation, the position of the photographic stop for the first photograph is determined during alignment from the information of whether the eye is the left eye or the right eye obtained from the right/left eye detector 70, the information of the fixation lamp position lighted in step S2, and the photography mode selected in step S3. After the focus has been adjusted, the photographic stop determined in such a manner is selected. For example, when the photographic stop thus determined is the photographic stop 31b, the movable stop unit 32 is moved in step S14 to the position of FIG. 3B to select the photographic stop 31b (step S14).

When the shutter switch 66 is operated in step S15, the strobe light emits light, the ocular fundus is photographed via the photographic stop 31b selected in step S14, a first ocular fundus image is acquired, and the image is associated with photographic conditions such as the position of the photographic stop 31b and recorded in the memory 61. Next, the process advances from step S19 to step S20. The photographic stop 31c that was not selected in step S14 is selected (step S20), the strobe light emits light (step S21), the ocular fundus is photographed by the CCD 41 via the photographic stop 31c, and a second ocular fundus image is acquired as a second image (step S22). Similar to the first ocular fundus image, the second ocular fundus image is associated with the position information of the photographic stop that was used when the image was acquired, and the image is recorded in the memory 61 (step S23).

Next, since the current mode is the stereoscopic photography mode, step S30 is affirmed, the process advances to step S35, and photography is ended.

In this manner, the photographic stops 31b and 31c (two-aperture stop) are switched in a single shutter operation (step S15) in stereoscopic photography, two ocular fundus images, i.e., left and right images for stereoscopic viewing, are consecutively taken, and the images are recorded together with the information of the photographic stop position (second or third position, or the left position, right position, and the like) at the time the images were acquired.

In the case of three consecutive images being photographed, the first photograph is taken via the photographic stop 31a in the same manner at the monocular photography, and the remaining two photographs are taken via the photographic stops 31b and 31c. After ocular fundus alignment has ended, the shutter switch 66 is operated in step S15, whereupon a strobe light is emitted and the ocular fundus is photographed via the photographic stop 31a. The first picture is recorded as a first image in the memory 61 with photography condition information such as the photographic stop position (steps S17 and S18). Next, one of the photographic stops 31b or 31c is selected (step S20), the strobe light is emitted again (step S21) and the ocular fundus is photographed via the selected photographic stop. The second picture is recorded in the memory 61 as a second image that is associated with photography condition information such as the position of the photographic stop (steps S22 and S23). The remaining photographic stop is then selected (step S31), the strobe light is emitted again (step S32), and the ocular fundus is photographed via the selected photographic stop. The third picture is recorded in the memory 61 as a third image that is associated with photography condition information such as the position of the photographic stop (steps S33 and S34).

In this manner, when three consecutive images are photographed, the images are consecutively photographed via the photographic stops 31a, 31b, and 31c in a sequential manner in a single shutter operation (step S15), and the images are recorded together with the information of the photographic stop position (first, second, or third position, or the center position, left position, right position, and the like) at the time the images were acquired.

In the present invention, since fluorescent photography can be performed in addition to color photography, the exciter filter 18 and the barrier filter 34 are inserted into the optical path when fluorescent photography is to be performed in each photography mode.

The image recorded in the memory 61 is transferred to an external recording apparatus 64 with a prescribed timing. At this point, the timing for transferring the image recorded in the memory 61 to the external recording apparatus 64 is varied depending on whether or not it is monocular color photography. For example, in modes other than monocular color photography, the images are stored in the memory 61 until a prescribed number of photographs is taken, and the images are thereafter sent to the external recording apparatus 64. During fluorescent photography, the image is converted to a black and white image in the control and computation unit 60, and the converted image is stored in the external recording apparatus 64.

When images recorded in the memory 61 or the external recording apparatus 64 are retrieved and displayed (step S36), the display method and display means (monitor) are varied in accordance with the photography mode (steps S37 to S39).

When the ocular fundus image photographed by monocular photography is displayed, the monitor 62 is automatically selected and the ocular fundus image is displayed on the monitor 62 as a still image with the photography condition information. When the two images, i.e., left and right images obtained in stereoscopic photography are retrieved and stereoscopically viewed, the stereo monitor 63 is used, the image associated with the information of the left position is displayed on the left side, the image associated with the information of the right position is arranged on the right side, and other photography condition information is also displayed together therewith.

Figure 7:
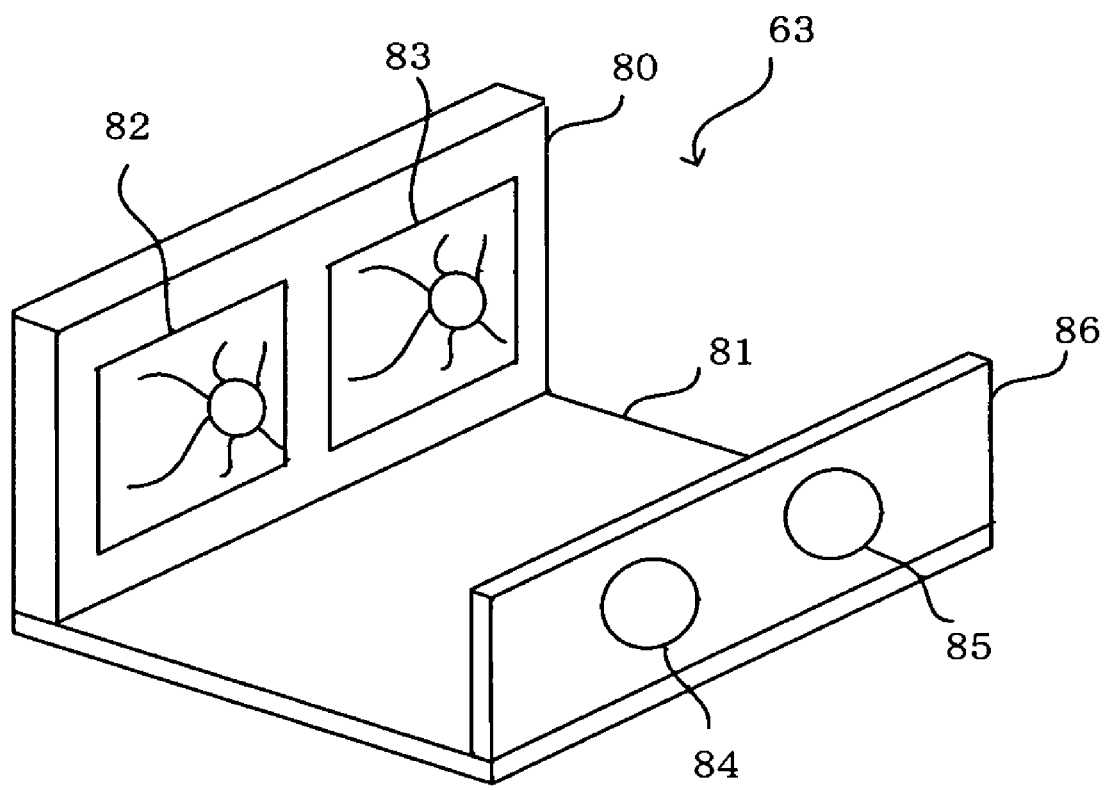
FIG. 7 is a perspective view showing the external appearance of a stereo monitor.

The stereo monitor 63 is shown in detail in FIG. 7. Mounted on a base 81 of the stereo monitor 63 is a display 80 on which the left and right images 82 and 83 that were photographed by switching the photographic stop are symmetrically arranged and displayed in a symmetrical fashion. Mounted on the base 81 is a stereoscope 86 composed of lenses or prisms 84 and 85 that are disposed apart from the display 80 by a distance suitable for stereoscopic viewing. During stereoscopic viewing, the examiner observes the image for the left eye (left image) 82 via the lens 84 using the left eye, and observes the image for the right eye (right image) via the lens 85 using the right eye. When an ordinary personal computer is operated, diagnosis can be performed with good efficiency while viewing the monitor 62 or otherwise properly using the monitors.

Figure 8:
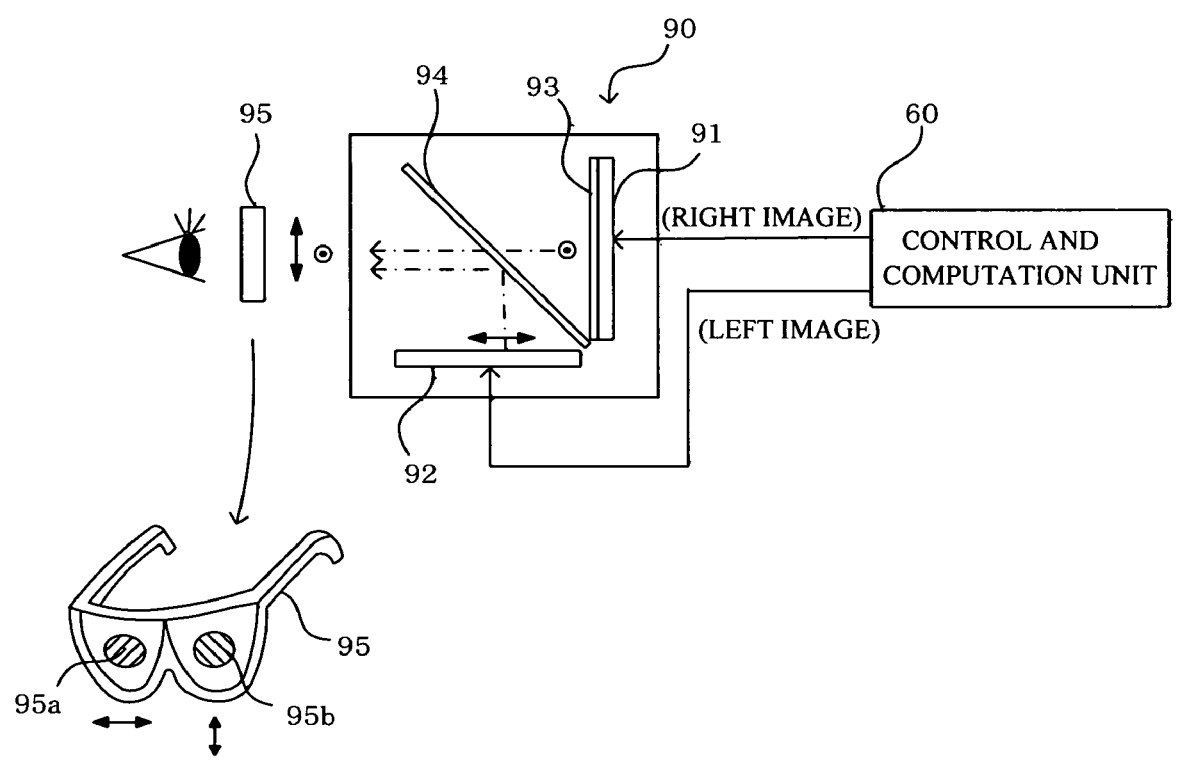
FIG. 8 is a block diagram showing another configuration of a stereo monitor.

The configuration of another stereo monitor 90 is shown in FIG. 8. The stereo monitor 90 includes two vertically polarized liquid crystal displays 91 and 92 that are disposed so as to be orthogonal. A half mirror 94 inclined at 45° is disposed therebetween. A wave plate 93 is disposed in a prescribed orientation on the front surface of the vertically disposed liquid crystal display 91 to convert the vertical polarization of the liquid crystal display 91 to horizontal polarization. The left image and the right image are inputted from the control and computation unit 60 to the liquid crystal displays 91 and 92, respectively. In such a case, the left image is reflected by the half mirror 94 and vertically inverted, so that the control and computation unit 60 performs vertical specular processing to output the vertically inverted image to the liquid crystal display 92. On the other hand, the right image is not outputted to the liquid crystal display 91 without being subjected to such processing. With such a stereo monitor, the right image is converted to horizontal polarization by way of the wave plate 93, is made incident on a half mirror 94, is optically combined with the vertically polarized left image, and is observed by the examiner who is wearing spectacles 95. A filter 95a for horizontally polarized light is fitted into to the right eye frame of the spectacles 95, and a filter 95b for vertically polarized light is fitted into the left eye frame. Therefore, the horizontally polarized right image is transmitted through only the filter 95a of the right eye frame, and the vertically polarized left image is transmitted through only the filter 95b of the left eye frame. The ocular fundus image can thereby be stereoscopically viewed because the examiner sees the right image with the right eye and the left image with the left eye.

In addition to aligning and displaying an image for the left eye and an image for the right eye described above, another possible method of performing stereoscopic viewing from a stereo image involves computationally processing the two images, and creating and displaying 3D data or combined stereographic images. Various methods of creating 3D data or stereographic images from stereo images have been proposed (JP-A 1996-567, JP-A 2002-34924, and the like). Various methods of displaying such data have also been proposed in JP-A 2001-42260, Japanese Publication of PCT International Application No. 2005-500578, and the like, and such methods have been implemented in commercial applications. Therefore, such methods can be selected, combined, and used as needed.

The 3D data, combined stereographic images and other data can be recorded and stored in association with the original image. This advantageously allows a computational operation to be omitted for each time of display.

The two images need be of relatively good quality when the two images, i.e., the left and right images, are stereoscopically viewed as described above. In fundus photography an examiner photographs the eye of a human subject, so that accurate, high-quality ocular fundus photography is not always carried out each examination due to blinking, poor fixation, and other subject-related problems, or due to improper photography operation by the examiner. It is very difficult to immediately align, display, and stereoscopically view poor-quality images, and such images cause the examiner discomfort. Such stereoscopic viewing may also lead to a misdiagnosis. When 3D data is computed or stereographic images are combined from poor-quality images, a good diagnostic result cannot also be obtained because of a reliability problem.

Figure 9:
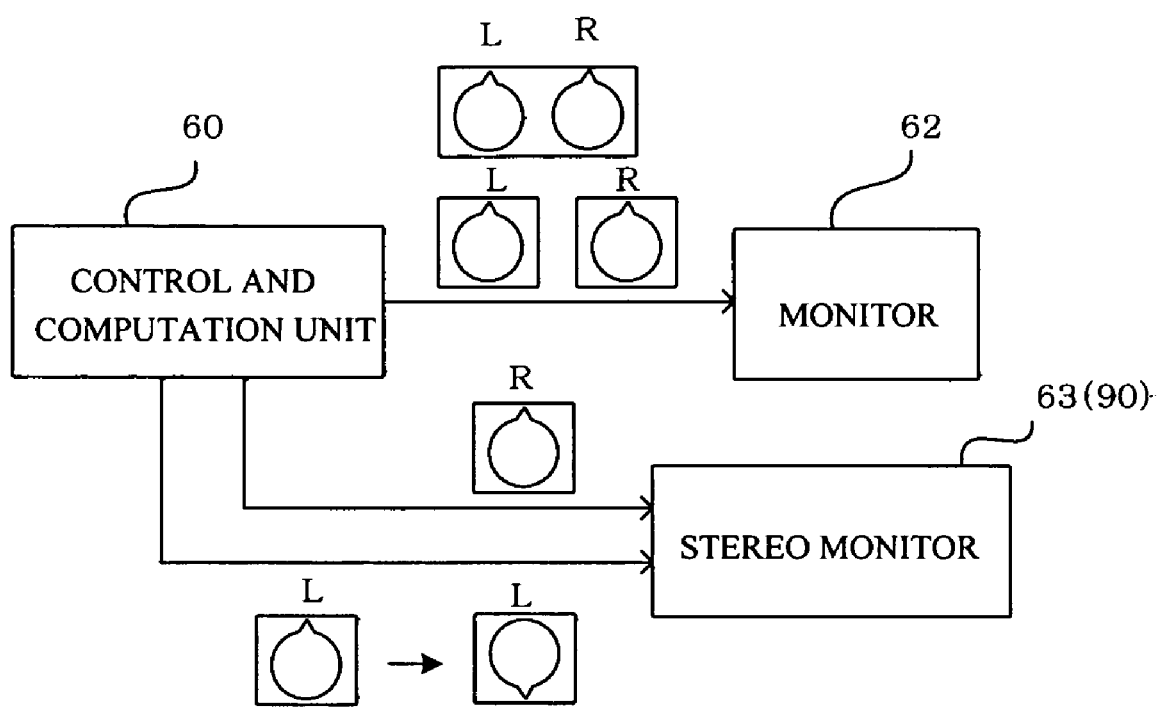
FIG. 9 is an illustrative view showing the state in which an image for stereoscopic viewing has been examined and is thereafter displayed on a stereo monitor.

In view of the above, the examiner preferably pre-checks the quality of the amount of flare, the focus, and the alignment for the two images. Examples of implementing such factors are shown in FIGS. 9 to 11

Figure 10:
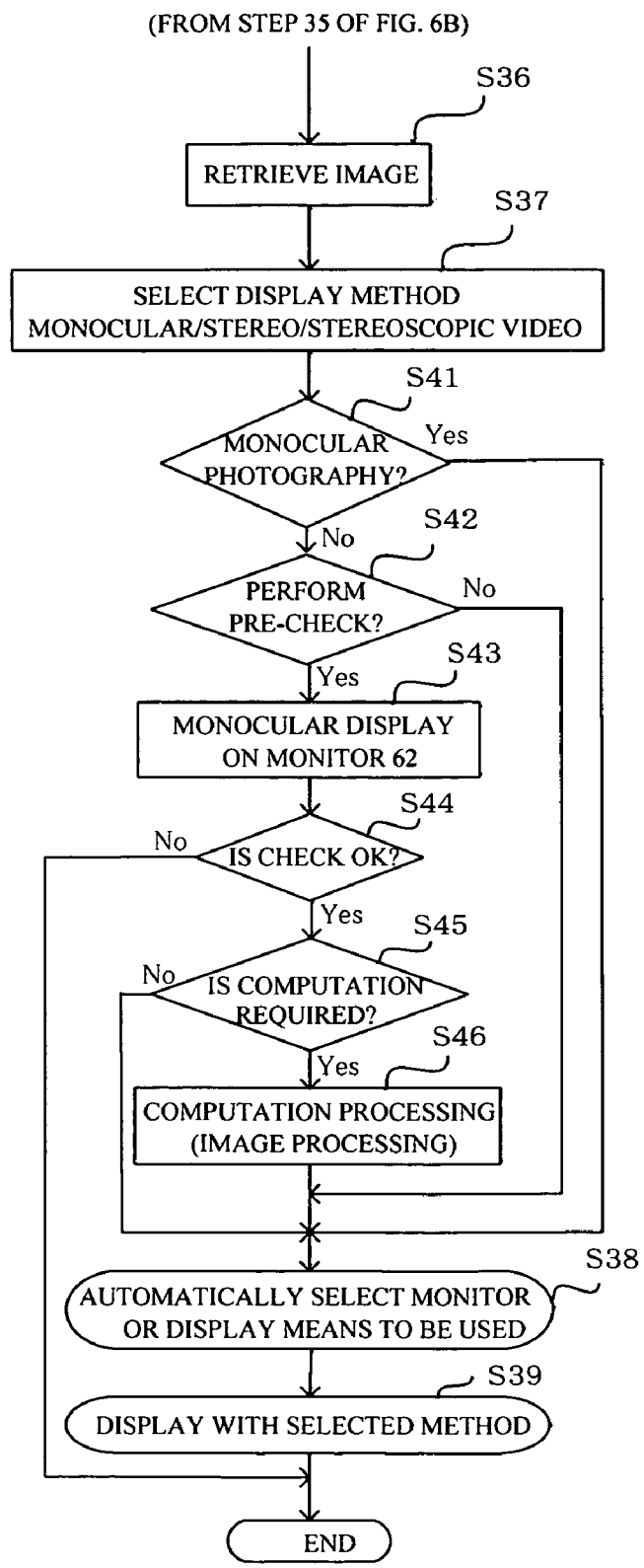
FIG. 10 is a flowchart showing another example of the sequence for displaying a fundus image.
Figure 11:
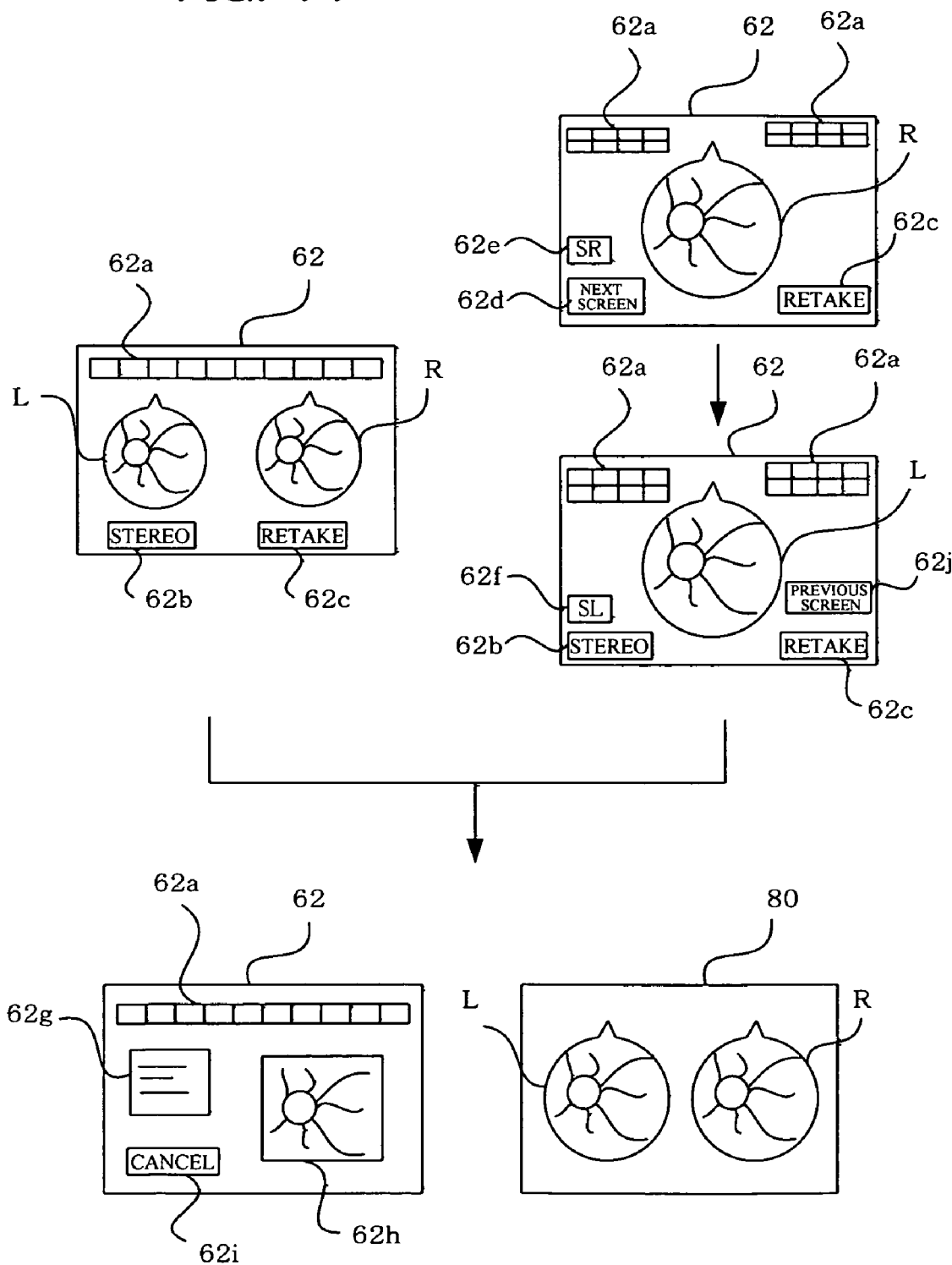
FIG. 11 is an illustrative view showing the sequence of checking and displaying the fundus image in stereo.

FIG. 10 shows the flow used when the two images are checked and displayed for stereoscopic viewing. The process through step S37 is the same as that through step S37 of FIG. 6B. The process advances to the same steps as steps S38 and S39 of FIG. 6B when it is determined that monocular photography is being performed (affirmative, in step S41). The monitor 62 is then selected for monocular display.

On the other hand, when a stereo image is acquired in the second photography mode and the stereo image displayed without being checked in advance (negative, in step S42), the process advances to steps S38 and S39, the stereo monitor 63 or 90 is selected, and the two images are displayed for stereoscopic viewing. Conversely, monocular display is carried out (step S43) using the monitor 62 when a pre-check is performed. This display is carried out by outputting the two images, i.e., the photographed right image R and left image L, from the control and computation unit 60 to the monitor 62, as shown in the upper part of FIG. 9. In this case, the examiner checks two images because the two images R and L are aligned and displayed below the toolbar 62a of the monitor 62 in the manner shown in the upper left part of FIG. 11.

When, as a result of the check, one or both of the two images are not good quality images (negative, in step S44), the photograph retake button 62c is clicked to retake the photograph. Conversely, if the two images are not failed photographic images, the stereo button 62b on the monitor 62 is clicked. This clicking action causes the left image L and the right image R to automatically move from the monitor 62 to the stereo monitor 63 or 90 and to be stereographically displayed on the stereo monitors 63 and 90. At this point, when the two images are computational processed to create and display the 3D data and combined stereographic images, the two images are subjected to prescribed computation in the control and computation unit 60 to carry out image processing (steps S45 and S46).

The display for stereoscopic viewing in the display 80 is shown in the lower right of the FIG. 11 for a case in which the stereo monitor 63 is used. Here, as shown in the lower left of FIG. 11, a screen 62g that shows the subject's data and the clinical record screen 62h are displayed on the monitor 62. In this case, the cancel button 62i is operated when the display for stereoscopic viewing is to be cancelled. It is to be noted that the left image L is subjected to specular processing in the manner indicated by the arrows in FIG. 9 when the stereo monitor 90 is used.

The display of the two images may be carried out by individually outputting the two images R and L to the monitor 62 in a sequential manner, as shown in the lower stage of FIG. 9. In this case, the right image R is first displayed on the monitor 62 in the upper right of FIG. 11, and "SR" 62e is displayed to indicate that the image is the right image R. If the image is not of good quality, the photograph retake button 62c is operated to retake the photograph. On the other hand, a next screen button 62d is operated when the image is of good quality, whereupon the left image L is displayed in the manner shown below, and "SL" 62f is displayed to indicate that the image is the left image. If the image is not of good quality, the photograph retake button 62c is clicked to retake the photograph. The previous screen button 62j is clicked when the operator desires to return to the previous screen and display of the right image R. The stereo button 62b is clicked when the image is of good quality, whereupon the process advances to display for stereoscopic viewing as described above. When two images are displayed in consecutive fashion, the photography condition information is displayed together on the monitor 62 in the same manner as monocular photography.

Since the tool bar 62a is displayed on the monitor 62 even after stereographic display on the stereo monitors 63 and 90, the screen operation is substantially carried out using the tool bar 62a on the monitor 62 rather than on the stereo monitors 63 and 90.

Such a configuration allows the left and right images to be displayed simultaneously or one by one on the monitor 62, and the photographer can confirm the quality of the images for stereoscopic observation. Therefore, a misdiagnosis or wasted examiner time caused by stereoscopic observation of poor-quality images can be prevented in advance.

The control and computation unit 60 may determine the quality of the left and right images in lieu of the photographer determining the quality of the images, and when the two images are determined to be of good quality, the images may be automatically outputted to the stereo monitors 63 and 90.

On the other hand, three images are repeatedly displayed one image at a time using the monitor 62 when the three images obtained by three consecutive photography are retrieved and displayed. This repeated display sequence creates a type of stereo video image. The case in which the two images obtained via the photographic stops 31b and 31c are displayed from among the three images is the same as the display of the images obtained in stereoscopic photography. Therefore, the image to which the information of the left position has been added is displayed as the left image, the image to which the information of the right position has been added is arranged on the right side as the right image, and other photography condition information is also displayed together using the stereo monitors 63 and 90. When the three images are each individually displayed, each image is displayed on the monitor 62 together with photography condition information in the same manner as monocular photography.

The greater spacing of the photographic stops 31b and 31c allows a larger parallax and better quality images for stereoscopic viewing. Therefore, the spacing of the photographic stops 31b and 31c may be adjusted in accordance with the diameter of the pupil because the diameter of the pupil is measured in step S8. A mydriatic agent is generally dropped on the eye in order to increase the diameter of the pupil of the subject's eye. In this case, the filter 13 is removed from the optical path to make observations and carry out alignment under visible light.

When the photographic stop position is varied to carry out photography as described above, the information of the photographic stop position is recorded in association with the image, and stereo analysis (analysis in the depth direction) of the ocular fundus image may be carried out based on the positional information.

The invention claimed is:

1. An ophthalmic photography apparatus comprising:
   imaging means including an objective lens for photographing a subject's eye as an electronic image via a photographic stop;
   recording means for recording a photographed subject-eye image; and
   selection means for switching the photographic stop and selecting a photographic stop that is in a different position,
   wherein the subject's eye is sequentially photographed in a single shutter operation via photographic stops that are in different positions to thereby acquire a plurality of images of the subject's eye, and each of the acquired subject-eye images is recorded in the recording means in association with the position of the photographic stop used when the image is acquired, and
   wherein one of the photographic stops is positioned on the optical axis of the objective lens and is selected during observation prior to photography, and during photography the photographic stop is selected which is determined in accordance with the selected photography mode.

2. An ophthalmic photography apparatus having first and second photography modes, comprising:

imaging means for photographing a subject's eye as an electronic image via a photographic stop; and selection means for switching the photographic stop and selecting a photographic stop that is in a different position, wherein, when the first photography mode has been selected, the subject's eye is photographed in a single shutter operation via the photographic stop that is in a first position to thereby acquire a single image of the subject's eye, and, when the second photography mode has been selected, the photographic stop that is in a second and third position is selected, and the subject's eye is photographed in a single shutter operation via selected one of photographic stops and subsequently via the other photographic stop to thereby acquire two images of the subject's eye.

3. An ophthalmic photography apparatus having first, second, and third photography modes, comprising:

imaging means for photographing a subject's eye as an electronic image via a photographic stop; and selection means for switching the photographic stop and selecting a photographic stop that is in a different position, wherein, when the first photography mode has been selected, the subject's eye is photographed in a single shutter operation via the photographic stop that is in a first position to thereby acquire a single image of the subject's eye; when the second photography mode has been selected, the photographic stop that is in a second and third position is selected, and the subject's eye is photographed in a single shutter operation via selected one of photographic stops and subsequently via the other photographic stop to thereby acquire two images of the subject's eye; and, when the third photography mode has been selected, the photographic stop that is in a first, second and third position is selected, and the subject's eye is photographed in a single shutter operation via selected one of photographic stops, subsequently via remaining one of photographic stops, and then via the other remaining photographic stop to thereby acquire three images of the subject's eye.

4. An ophthalmic photography apparatus according to claim 2 or 3, wherein the first to third positions are substantially conjugate with the anterior ocular segment of the subject's eye, the first position is a position in which the center of the photographic stop in the first position coincides with the optical axis of the photographic optical system, and the second and third positions are positions conjugate with the anterior ocular segment and positions in which a photographic optical path is divided into left and right in order to obtain left and right images for stereoscopic viewing.

5. An ophthalmic photography apparatus according to claim 2 or 3, wherein acquired images of the subject's eye are recorded in association with the position of the photographic stop used when the images were acquired.

6. An ophthalmic photography apparatus according to claim 2 or 3, wherein the display method for the image of the photographed subject's eye is different in the first photography mode from that in other modes.

7. An ophthalmic photography apparatus according to claim 6, wherein the two images of the subject's eye that were acquired in the second photography mode are displayed side by side.

8. An ophthalmic photography apparatus according to claim 6, wherein the two images of the subject's eye that were acquired in the second photography mode are subjected to image processing due to prescribed computation, and the two images of the subject's eye are displayed on a dedicated stereoscopic image display apparatus.

9. An ophthalmic photography apparatus according to claim 8, wherein the two images of the subject's eye that were acquired in the second photography mode are automatically displayed side by side on a first display apparatus, and a prescribed operation is performed to display the two images of the subject's eye on a second display apparatus.

10. An ophthalmic photography apparatus according to claim 9, wherein the second display apparatus is a stereoscopic image display apparatus, and the two images of the subject's eye acquired in the second photography mode are subjected to image processing due to prescribed computation and displayed on the second display apparatus.

11. An ophthalmic photography apparatus according to claim 3, wherein the three images of the subject's eye acquired in the third photography mode are repeatedly displayed one image at a time.

12. An ophthalmic photography apparatus according to any one of claims 1, 2 and 3, further including first recording means for recording images of the subject's eye and second recording means for recording images transferred from the first recording means at a lower speed than the first recording means, and the transfer timing of images from the first recording means to the second recording means differs depending on the photography mode.

13. An ophthalmic photography apparatus according to any one of claims 1, 2 and 3, further including an illumination stop that is provided in a substantially conjugate position to the anterior ocular segment inside the illumination optical system and that is switched in conjunction with the switching of the photographic stop.

14. An ophthalmic photography apparatus according to any one of claims 2 and 3, wherein one of the photographic stops is positioned on the optical axis of the objective lens and is selected during observation prior to photography, and during photography the photographic stop is selected which is respectively determined in accordance with the photography modes.

15. An ophthalmic photography apparatus according to claim 14, wherein the position of the photographic stop prior to shutter operation is determined in accordance with the photography mode and the position of the internal fixation lamp used during observation.

16. An ophthalmic photography apparatus according to claim 15, wherein detection means for detecting whether the subject's eye to be photographed is the right eye or the left eye is provided, and the position of the photographic stop prior to shutter operation is determined in accordance with the photography mode, the position of the internal fixation lamp used during observation, and the detection result produced by the detection means.

17. An ophthalmic photography apparatus according to claim 15, wherein the position of the photographic stop immediately after shutter operation is the position of the photographic stop used during alignment observation.

18. An ophthalmic photography apparatus according to any one of claim 1, 2 or 3 wherein an optical element that directs a focus marker to the subject's eye is inserted into and removed from the optical path in conjunction with the switching of the photographic stop.

19. An ophthalmic photography apparatus according to claim 3, wherein the spacing of the photographic stops in the second and third positions is adjustable.

20. An ophthalmic photography apparatus according to claim 19, wherein the spacing of the photographic stop in the second and third positions is adjusted in accordance with the diameter of the pupil.

21. An ophthalmic photography apparatus according to claim 19 or 20, wherein position information of the photographic stop is recorded and stored as photography condition information in association with the acquired image of the subject's eye, and the depth direction of the image is analyzed based on the position information.

\* \* \* \* \*